(12) United States Patent
Vogel et al.

(10) Patent No.: US 8,207,371 B2
(45) Date of Patent: Jun. 26, 2012

(54) PROCESS FOR PREPARING (METH)ACRYLIC ACID

(75) Inventors: Bernd Vogel, Wiesbaden (DE); Alexander May, Darmstadt (DE); Hermann Siegert, Seeheim-Jugenheim (DE)

(73) Assignee: Evonik Röhm GmbH, Darmstadt (DE)

( * ) Notice: Subject to any disclaimer, the term of this patent is extended or adjusted under 35 U.S.C. 154(b) by 55 days.

(21) Appl. No.: 12/442,415

(22) PCT Filed: Aug. 30, 2007

(86) PCT No.: PCT/EP2007/059029
§ 371 (c)(1), (2), (4) Date: Mar. 23, 2009

(87) PCT Pub. No.: WO2008/061819
PCT Pub. Date: May 29, 2008

(65) Prior Publication Data
US 2010/0029979 A1    Feb. 4, 2010

(30) Foreign Application Priority Data
Nov. 22, 2006 (DE) .................. 10 2006 055 428

(51) Int. Cl.
*C07C 67/30* (2006.01)
*C07C 35/00* (2006.01)

(52) U.S. Cl. ........................................ 560/212; 562/599

(58) Field of Classification Search .................. None
See application file for complete search history.

(56) References Cited

U.S. PATENT DOCUMENTS

| | | |
|---|---|---|
| 3,562,320 A | 2/1971 | Woodward |
| 3,666,805 A * | 5/1972 | Volker et al. ................ 562/599 |
| 6,743,407 B2 | 6/2004 | Schaefer et al. |
| 6,977,310 B2 | 12/2005 | Ackermann et al. |
| 6,979,432 B2 | 12/2005 | Schaefer et al. |
| 7,288,402 B2 | 10/2007 | Osswald et al. |
| 7,491,521 B2 | 2/2009 | Osswald et al. |
| 2006/0211880 A1 | 9/2006 | Ackermann et al. |
| 2008/0194862 A1 | 8/2008 | Ackermann et al. |
| 2008/0194875 A1 | 8/2008 | Ackermann et al. |
| 2008/0248538 A1 | 10/2008 | Osswald et al. |
| 2008/0269431 A1 | 10/2008 | Sarcinelli et al. |
| 2009/0118533 A1 | 5/2009 | Broell et al. |
| 2011/0034728 A1 | 2/2011 | May et al. |
| 2011/0306784 A1 | 12/2011 | May et al. |

FOREIGN PATENT DOCUMENTS

| | | |
|---|---|---|
| DE | 1 768 253 | 10/1971 |
| WO | 2005 095320 | 10/2005 |

OTHER PUBLICATIONS

U.S. Appl. No. 12/298,034, filed Oct. 22, 2008, May, et al.
U.S. Appl. No. 12/300,189, filed Nov. 10, 2008, Broell, et al.
U.S. Appl. No. 12/299,217, filed Oct. 31, 2008, Broell, et al.
U.S. Appl. No. 12/307,773, filed Jan. 7, 2009, Ackermann, et al.
U.S. Appl. No. 12/441,145, filed Mar. 13, 2009, May, et al.
U.S. Appl. No. 12/515,036, filed May 15, 2009, May, et al.
U.S. Appl. No. 12/443,784, filed Mar. 31, 2009, Vogel, et al.
U.S. Appl. No. 12/303,161, filed Dec. 2, 2008, Marx, et al.
Obmelyukhina et al., "By-Products from the Industrial Synthesis of Methacrylic Acid", J Appl Chem USSR, vol. 53, No. 2, pp. 358-362, XP009093039, (1980).
U.S. Appl. No. 12/593,090, filed Sep. 25, 2009, Marx, et al.
U.S. Appl. No. 12/602,593, filed Dec. 1, 2009, Marx, et al.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to a process for preparing (meth)acrylic acid, characterized in that a cyclic ester is converted to (meth)acrylic acid in the presence of a catalyst. The (meth)acrylic acid prepared can in particular be converted to (meth)acrylates.

12 Claims, No Drawings

PROCESS FOR PREPARING (METH)ACRYLIC ACID

The present invention relates to processes for preparing (meth)acrylic acid.

The preparation of (meth)acrylic acid is established prior art, different methods being employed to obtain (meth)acrylic acid.

For example, α-hydroxyisobutyric acid can serve as a starting material for preparing methacrylic acid. Such a process is described, for example, in U.S. Pat. No. 3,487,101, where the preparation of various methacrylic acid derivatives, especially methacrylic acid and meth-acrylic esters, starting from 2-hydroxyisobutyric acid in the liquid phase, is characterized in that the conversion of HIBA to methacrylic acid is performed in the presence of a dissolved basic catalyst at high temperatures between 180° C.-320° C. in the presence of high-boiling esters (e.g. dimethyl phthalate) and internal anhydrides (e.g. phthalic anhydride). According to the patent, MAA selectivities around 98% are achieved at HIBA conversions of >90%. No statements are made about the long-term stability of the liquid catalyst solution, especially the exhaustion of the anhydride used.

DE-A 1 191367 relates to the preparation of methacrylic acid (MAA) starting from α-hydroxyisobutyric acid (HIBA) in the liquid phase, characterized in that the conversion of HIBA to methacrylic acid is performed in the presence of polymerization inhibitors (for example copper powder) and in the presence of a catalyst mixture consisting of metal halides and alkali metal halides at high temperatures between 180° C.-220° C. According to the patent, MAA selectivities of >99% are achieved at HIBA conversions of >90%. The best results are achieved with catalyst mixtures of zinc bromide and lithium bromide. It is common knowledge that the use of halide catalysts at high temperatures places severe demands on the materials to be used, and these problems regarding the entrained halogenated by-products present in the distillate also occur in downstream plant parts.

EP 0 487 853 describes the preparation of methacrylic acid starting from acetone cyanohydrin (ACH), characterized in that, in the first step, ACH is reacted with water at moderate temperatures in the presence of a heterogeneous hydrolysis catalyst and, in the second step, α-hydroxyisobutyramide is reacted with methyl formate or methanol/carbon monoxide to form formamide and methyl hydroxyisobutyrate (MHIB), and, in the third step, MHIB is hydrolysed in the presence of a heterogeneous ion exchanger with water to give hydroxyisobutyric acid, and, in the fourth step, HIBA is dehydrated by allowing it to react in the liquid phase at high temperatures in the presence of a soluble alkali metal salt. The methacrylic acid preparation ex HIBA is described with more or less quantitative selectivities at high conversions around 99%. The multitude of reaction steps necessary and the necessity of intermediate isolation of individual intermediates, especially also the performance of individual process steps at elevated pressure, make the process complicated and hence ultimately uneconomic. Furthermore, formamide is necessarily prepared, this compound in many cases being considered to be an undesired by-product which has to be disposed of in an expensive manner.

DE-A 1 768 253 describes a process for preparing methacrylic acid by dehydrating α-hydroxyisobutyric acid (HIBA), characterized in that HIBA is reacted in the liquid phase at a temperature of at least 160° C. in the presence of a dehydration catalyst which consists of a metal salt of alpha-hydroxyisobutyric acid. In this case, the alkali metal and alkaline earth metal salts of HIBA are particularly suitable, which are prepared in situ by conversion of suitable metal salts in an HIBA melt. According to the patent, MAA yields up to 95% ex HIBA are described, the feed of the continuous procedure consisting of HIBA and approx. 1.5% by weight of HIBA alkali metal salt.

RU 89631 relates to a process for preparing methacrylic acid starting from 2-hydroxyisobutyric acid by water elimination in the liquid phase, characterized in that the reaction is performed in the absence of a catalyst with an aqueous solution of HIBA (up to 62% by weight of HIBA in water) under pressure at high temperatures of 200° C.-240° C.

In addition, there has been intensive investigation of the use of propene as the base raw material, methacrylic acid being obtained in moderate yields via the stages of hydrocarbonylation (to isobutyric acid) and dehydrogenating oxidation.

It is known that propanol or propionic acid, which are obtainable in industrial processes starting from ethylene and C-1 units such as carbon monoxide, can be used as the base raw material. In these processes, an aldolizing reaction is effected with formaldehyde with dehydration of the β-hydroxycarbonyl compound formed in situ to give the corresponding α,β-unsaturated compound. An overview of the common processes for preparing methacrylic acid and its esters can be found in the literature, such as Weissermel, Arpe "Industrielle organische Chemie", VCH, Weinheim 1994, 4th edition, p. 305 ff., or Kirk Othmer "Encyclopedia of Chemical Technology", 3rd edition, Vol. 15, page 357.

(Meth)acrylic acid serves in many cases as a comonomer for preparing a multitude of polymers. For this purpose, relatively small amounts of (meth)acrylic acid are required. For economic reasons, these small amounts do not justify the building of large production plants which are needed to prepare (meth)acrylic acid by oxidation of hydrocarbons or from ACH.

There is therefore the need to transport (meth)acrylic acid. However, the transport of (meth)acrylic acid is very complicated, since (meth)acrylic acid polymerizes very easily. Thus (meth)acrylic acid forms polymers rapidly in the course of storage in solid form or at high temperatures. Therefore, (meth)acrylic acids have to be transported within a relatively narrow temperature window in order to prevent polymerization. In many cases, polymerization inhibitors are used, which, however, in many cases have to be removed before use.

In addition, as already detailed, (meth)acrylic acids may be obtained from α-hydroxycarboxylic acids. Accordingly, it would be possible, for example, to transport α-hydroxyisobutyric acid in order to prepare methacrylic acid therefrom at the point of use. However, a disadvantage here is the high transport costs which are attributable to the higher molecular weight of α-hydroxyisobutyric acid in comparison to methacrylic acid. In addition, both (meth)acrylic acids and α-hydroxycarboxylic acids require acid-resistant transport vessels. The transport of these compounds is therefore complicated and thus expensive.

In view of the prior art, it is thus an object of the present invention to provide processes for preparing (meth)acrylic acid which can be performed in a particularly simple and inexpensive manner and with high yield. At the same time, it should also be particularly economically viable to obtain small amounts. A particular problem has more particularly been to provide a process whose starting materials can be transported easily and safely.

Furthermore, it was accordingly an object of the present invention to provide a process for preparing (meth)acrylic acid in which only a small amount of by-products is obtained.

At the same time, the product should as far as possible be obtained in high yields and, viewed overall, with low energy consumption.

This object and further objects which are not stated explicitly but which can be derived or discerned from the connections discussed herein by way of introduction are achieved by a process having all features of Claim 1. Appropriate modifications of the processes according to the invention are protected in subclaims.

By converting a cyclic ester to (meth)acrylic acid in the presence of a catalyst, it is possible to provide a process for preparing (meth)acrylic acid which can be performed in a particularly simple and inexpensive manner and with high yield.

At the same time, the processes according to the invention can achieve a series of further advantages. One is that the starting material used can be transported easily, safely and inexpensively. This allows (meth)-acrylic acid to be provided inexpensively for the production of copolymers without any need to build and finance an expensive production plant which affords (meth)acrylic acid from ACH or by oxidation of hydrocarbons. In addition, only small amounts of by-products are obtained, the product being obtained in high yields and, viewed overall, with low energy consumption.

To prepare (meth)acrylic acid, a cyclic ester is reacted in the process according to the invention. Cyclic esters usable for this purpose are known per se. In the context of the present invention, the term "cyclic esters" denotes annular diesters which are obtained, for example, by dimerizing α-hydroxycarboxylic acids and/or α-hydroxycarboxylic esters.

In general, it is assumed that these esters correspond to the formula (I)

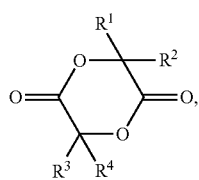

(I)

in which the $R^1$, $R^2$, $R^3$ and $R^4$ radicals are each independently hydrogen or a group having 1 to 30 carbon atoms, which in particular comprises 1-20, preferably 1-10, in particular 1-5 and more preferably 1-2 carbon atoms.

The expression "group having 1 to 30 carbon atoms" denotes radicals of organic compounds having 1 to 30 carbon atoms. In addition to aromatic and heteroaromatic groups, it also encompasses aliphatic and hetero-aliphatic groups, for example alkyl, cycloalkyl, alkoxy, cycloalkoxy, cycloalkylthio and alkenyl groups. The groups mentioned may be branched or unbranched.

According to the invention, aromatic groups denote radicals of mono- or polycyclic aromatic compounds having preferably 6 to 20, in particular 6 to 12 carbon atoms.

Heteroaromatic groups denote aryl radicals in which at least one CH group has been replaced by N and/or at least two adjacent CH groups have been replaced by S, NH or O.

The preferred alkyl groups include the methyl, ethyl, propyl, isopropyl, 1-butyl, 2-butyl, 2-methylpropyl, tert-butyl, pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and the eicosyl group.

The preferred cycloalkyl groups include the cyclopropyl, cyclobutyl, cyclopentyl, cyclohexyl, cycloheptyl and the cyclooctyl group, which are optionally substituted by branched or unbranched alkyl groups.

The preferred alkenyl groups include the vinyl, allyl, 2-methyl-2-propenyl, 2-butenyl, 2-pentenyl, 2-decenyl and the 2-eicosenyl group.

The R radicals may have substituents. The preferred substituents include halogens, especially fluorine, chlorine, bromine, and alkoxy groups.

The preferred cyclic esters include 1,4-dioxane-2,5-dione (glycolide), 3,6-dimethyl-1,4-dioxane-2,5-dione (lactide) or 3,6-dimethyl-1,4-dioxane-2,5-dione (tetramethylglycolide).

According to the invention, the process affords (meth) acrylic acid. In addition to acrylic acid (propenoic acid) and methacrylic acid (2-methylpropenoic acid), this includes in particular derivatives which comprise substituents. The suitable substituents include in particular halogens, such as chlorine, fluorine and bromine, and alkyl groups which may preferably comprise from 1 to 10, more preferably from 1 to 4 carbon atoms. These include β-methylacrylic acid (butenoic acid), α,β-dimethylacrylic acid, β-ethylacrylic acid and β,β-dimethylacrylic acid. Preference is given to acrylic acid (propenoic acid) and methacrylic acid (2-methylpropenoic acid), particular preference being given to methacrylic acid.

The cyclic ester can be converted, for example, in the gas phase or in the liquid phase. Preference is given to effecting the reaction in the liquid phase. In this case, the resulting (meth)acrylic acid can be removed from the reaction mixture preferably via the gas phase. For example, the cyclic ester can be heated in a still and the (meth)acrylic acid formed can be removed via the top and condensed. The reaction can be effected with or without solvent.

The solvents can serve in particular to facilitate the heating of the starting compounds in order to avoid overheating and associated by-product formation. The solvent can be removed from the mixture after heating the mixture to a temperature above the melting temperature of the starting material, before the cyclic ester is converted to (meth)acrylic acid. In addition, solvents can be used to keep the temperature of the reactant mixture low on addition to a reactor, especially a still. This may be appropriate especially in continuous processes. In addition, this allows the temperature to be kept low at the start of the reaction, so that particularly low proportions of undesired by-products are formed. Solvents having a low boiling point can be removed via the top in the case of a reaction in a still. Solvents having high boiling points remain in the bottoms in many cases in the case of a reaction in a still. These solvents can be discharged from the bottom and used again to lower the liquefaction temperature of the starting compounds.

The suitable solvents include, for example, alcohols, ketones, aldehydes, esters, ethers, carboxylic acids, hydrocarbons and mixtures of these solvents with one another and with further solvents.

The hydrocarbon solvents include aliphatic, alicyclic and aromatic hydrocarbons. These hydrocarbons include pentane, hexane, especially n-hexane and 3-methyl-pentane, heptane, especially n-heptane and 3-methyl-hexane, octane, cyclopentane, cyclohexane, benzene, toluene, xylene, ethylbenzene.

In addition, the suitable solvents include carboxylic acids and carboxylic esters. These include in particular acetic acid, ethyl acetate, α-hydroxycarboxylic acids, especially 2-hydroxyisobutyric acid and methyl 2-hydroxyisobutyrate.

The ketones usable as solvents include, for example, acetone, methyl ethyl ketone, diethyl ketone, methyl propyl ketone, methyl isopropyl ketone, methyl butyl ketone, methyl 1-methylpropyl ketone, methyl 2-methylpropyl ketone, ethyl propyl ketone and other ketones having 2 or more carbon atoms in each case, preferably 4 to 12 and more preferably 4 to 9 carbon atoms.

The aldehydes usable as solvents include, for example, acetaldehyde, propionaldehyde, butyraldehyde, valeraldehyde, benzaldehyde and other aldehydes having 2 or more carbon atoms in each case, preferably 4 to 12 and more preferably 4 to 9 carbon atoms.

The ethers usable as solvents include diethyl ether, di-n-propyl ether, diisopropyl ether, di-n-butyl ether, diisobutyl ether and other ethers having in each case 2 or more carbon atoms, preferably 4 to 12 and more preferably 4 to 9 carbon atoms.

Alcohols may be used with particular preference as solvents. The preferred alcohols include alcohols having at least one carbon atom in each case, preferably 2 to 12 and more preferably 4 to 9 carbon atoms. The alcohols may have a linear, branched or cyclic structure. In addition, the alcohols may comprise aromatic groups or substituents, for example halogen atoms. The preferred alcohols include in particular methanol, ethanol, n-propanol, isopropanol, n-butanol, 1-methylpropanol, 2-methylpropanol, tert-butanol, n-pentanol, 1-methylbutanol, 2-methylbutanol, 3-methylbutanol, 2,2-dimethylpropanol, n-hexanol, 1-methylpentanol, 2-methylpentanol, 3-methylpentanol, 4-methylpentanol, 1,1-dimethylbutanol, 2,2-dimethylbutanol, 3,3-dimethylbutanol, 1,2-dimethylbutanol, n-heptanol, 1-methylhexanol, 2-methylhexanol, 3-methylhexanol, 4-methylhexanol, 1,2-dimethylpentanol, 1,3-dimethylpentanol, 1,1-dimethylpentanol, 1,1,2,2-tetramethylpropanol, benzyl alcohol, n-octanol, 2-ethylhexanol, n-nonanol, 1-methyloctanol, 2-methyloctanol, n-decanol, n-undecanol, 1-methyldecanol, 2-methyldecanol, n-dodecanol, 2,4-diethyloctanol, cyclopentanol, cyclohexanol, 4-tert-butylcyclohexanol, cycloheptanol, cyclododecanol, 2-(dimethylamino)ethanol, 3-(dimethylamino)propanol, 4-(dimethylamino)butanol, 5-(dimethylamino)pentanol, 6-(dimethylamino)hexanol, 8-(dimethylamino)octanol, 10-(dimethylamino)decanol, 12-(dimethylamino)dodecanol, 2-(diethylamino)ethanol, 3-(diethylamino)propanol, 4-(diethylamino)butanol, 5-(diethylamino)pentanol, 6-(diethylamino)hexanol, 8-(diethylamino)octanol, 10-(diethylamino)decanol, 12-(diethylamino)dodecanol, 2-(di(isopropyl)amino)ethanol, 3-(di(isopropyl)amino)propanol, 4-(di(isopropyl)amino)butanol, 5-(di(isopropyl)amino)pentanol, 6-(di(isopropyl)amino)hexanol, 8-(di(isopropyl)amino)octanol, 10-(di(isopropyl)amino)decanol, 12-(di(isopropyl)amino)dodecanol, 2-(dibutylamino)ethanol, 3-(dibutylamino)propanol, 4-(dibutylamino)butanol, 5-(dibutylamino)pentanol, 6-(dibutylamino)hexanol, 8-(dibutylamino)octanol, 10-(dibutylamino)decanol, 12-(dibutylamino)dodecanol, 2-(dihexylamino)ethanol, 3-(dihexylamino)propanol, 4-(dihexylamino)butanol, 5-(dihexylamino)pentanol, 6-(dihexylamino)hexanol, 8-(dihexylamino)octanol, 10-(dihexylamino)decanol, 12-(dihexylamino)dodecanol, 2-(methylethylamino)ethyl, 2-(methylpropylamino)ethanol, 2-(methylisopropyl)ethanol, 2-(methylbutylamino)ethanol, 2-(methylhexylamino)ethanol, 2-(methyloctylamino)ethanol, 2-(ethylpropylamino)ethanol, 2-(ethylisopropylamino)ethanol, 2-(ethylbutylamino)ethanol, 2-(ethylhexylamino)ethanol, 2-(ethyloctylamino)ethanol, 3-(methylethylamino)propanol, 3-(methylpropylamino)propanol, 3-(methylisopropylamino)propanol, 3-(methylbutylamino)propanol, 3-(methylhexylamino)propanol, 3-(methyloctylamino)propanol, 3-(ethylpropylamino)propanol, 3-(ethylisopropylamino)propanol, 3-(ethylbutylamino)propanol, 3-(ethylhexylamino)propanol, 3-(ethyloctylamino)propanol, 4-(methylethylamino)butanol, 4-(methylpropylamino)butanol, 4-(methylisopropylamino)butanol, 4-(methylbutylamino)butanol, 4-(methylhexylamino)butanol, 4-(methyloctylamino)butanol, 4-(ethylpropylamino)butanol, 4-(ethylisopropylamino)butanol, 4-(ethylbutylamino)butanol, 4-(ethylhexylamino)butanol, 4-(ethyloctylamino)butanol, 2-(n-piperidinyl)ethanol, 3-(N-piperidinyl)propanol, 4-(N-piperidinyl)butanol, 5-(N-piperidinyl)pentanol, 6-(N-piperidinyl)hexanol, 8-(N-piperidinyl)octanol, 10-(N-piperidinyl)decanol, 12-(N-piperidinyl)dodecanol, 2-(N-pyrrolidinyl)ethanol, 3-(N-pyrrolidinyl)propanol, 4-(N-pyrrolidinyl)butanol, 5-(N-pyrrolidinyl)pentanol, 6-(N-pyrrolidinyl)hexanol, 8-(N-pyrrolidinyl)octanol, 10-(N-pyrrolidinyl)decanol, 12-(N-pyrrolidinyl)dodecanol, 2-(N-morpholino)ethanol, 3-(N-morpholino)propanol, 4-(N-morpholino)butanol, 5-N-morpholino)pentanol, 6-(N-morpholino)hexanol, 8-(N-morpholino)octanol, 10-(N-morpholino)decanol, 12-(N-morpholino)dodecanol, 2-(N'-methyl-N-piperazinyl)ethanol, 3-(N'-methyl-N-piperazinyl)propanol, 4-(N'-methyl-N-piperazinyl)butanol, 5-(N'-methyl-N-piperazinyl)pentanol, 6-(N'-methyl-N-piperazinyl)hexanol, 8-(N'-methyl-N-piperazinyl)octanol, 10-(N'-methyl-N-piperazinyl)decanol, 12-(N'-methyl-N-piperazinyl)dodecanol, 2-(N'-ethyl-N-piperazinyl)ethanol, 3-(N'-ethyl-N-piperazinyl)propanol, 4-(N'-ethyl-N-piperazinyl)butanol, 5-N'-ethyl-N-piperazinyl)pentanol, 6-(N'-ethyl-N-piperazinyl)hexanol, 8-(N'-ethyl-N-piperazinyl)octanol, 10-(N'-ethyl-N-piperazinyl)decanol, 12-(N'-ethyl-N-piperazinyl)dodecanol, 2-(N'-isopropyl-N-piperazinyl)ethanol, 3-(N'-isopropyl-N-piperazinyl)propanol, 4-(N'-isopropyl-N-piperazinyl)butanol, 5-(N'-isopropyl-N-piperazinyl)pentanol 6-(N'-isopropyl-N-piperazinyl)hexanol, 8-(N'-isopropyl-N-piperazinyl)octanol, 10-(N'-isopropyl-N-piperazinyl)decanol, 12-(N'-isopropyl-N-piperazinyl)dodecanol, 3-oxabutanol, 3-oxapentanol, 2,2-dimethyl-4-oxapentanol, 3,6-dioxaheptanol, 3,6-dioxaoctanol, 3,6,9-trioxadecanol, 3,6,9-trioxaundecanol, 4-oxapentanol, 4-oxahexanol, 4-oxaheptanol, 4,8-dioxanonanol, 4,8-dioxadecanol, 4,8-dioxaundecanol, 5-oxahexanol or 5,10-dioxaundecanol.

In addition, ethoxylated and/or propoxylated alcohols and mixed ethoxylated/propoxylated alcohols may be used as solvents, in particular $R^5$—(O—$CH_2$—$CH_2$)$_x$—OH or
$R^5$—(O—CH($CH_3$)—$CH_2$)$_x$—OH, and/or $R^5$—(O—$CH_2$—CH($CH_3$))$_x$—OH, in which
$R^5$ is $C_1$ to $C_{20}$-alkyl and
x is an integer from 10 to 20,
or ethoxylated and/or propoxylated amino alcohols, for example
$R^6_2$N(—$CH_2$—$CH_2$—O)$_y$—H or $R^6_2$N(—CH($CH_3$)—$CH_2$—O)$_y$—H and/or $R^6_2$N(—$CH_2$CH($CH_3$)—O)$_y$—H,
in which y is an integer from 1 to 4. $R^6$ is an alkyl group having 1-6 carbon atoms, where the nitrogen with the substituents $R^6$ may also form a five- to seven-membered ring. The ring may optionally also be substituted by one or more short-chain alkyl groups, for example methyl, ethyl or propyl.

The solvents may be removed, for example, by distillation. These solvents, especially the alcohols, may preferably be withdrawn from the reaction mixture together with the (meth)acrylic acid obtained via the top of a still. The mixture thus obtained can subsequently be converted to the corresponding (meth)acrylate. Accordingly, the present invention also provides a process for preparing esters of (meth)acrylic acid, also known as (meth)acrylates. The esterification of (meth)acrylic acid with alcohols has been known for some time and is detailed, for example, in Ullmann's Encyclopaedia of Industrial Chemistry, 5th edition on CD-ROM.

The cyclic ester is converted in the presence of a catalyst. Catalysts suitable for this purpose are known per se and are detailed, for example, in DE-A 10 33 656, DE-A 10 62 696, FR 12 15 701, DE 630 020, DE 665 369, FR 10 80 212, DE 11 91 367 B1 and DE-A 17 68 253. For example, these catalysts may comprise acidic organic phosphates which are applied to silica supports or graphite supports. The catalysts to be used more preferably comprise at least one metal salt. These include in particular the salts detailed in the publications DE 11 91 367 B1 and DE-A 17 68 253. For example, salts of zinc, iron, tin, lead may be used. The particularly preferred metal salts include in particular alkali metal and/or alkaline earth metal salts. For example, a salt of a carboxylic acid having 1 to 10 carbon atoms, a carbonate salt, a hydroxide, an oxide, a halogen salt or a sulphite salt may be used. The particularly preferred carboxylic acids whose salts may be used as the catalyst include (meth)acrylic acid, α-hydroxycarboxylic acids, especially hydroxyacetic acid (glycolic acid), 2-hydroxypropionic acid (lactic acid) and/or 2-hydroxyisobutyric acid, and also acetic acid, propionic acid, butanoic acid, pentanoic acid, hexanoic acid, heptanoic acid, octanoic acid and/or nonanoic acid. The catalysts detailed above may be used individually or as a mixture. For example, mixtures of halides of zinc, of iron, of tin and of lead with alkali metal and/or alkaline earth metal halides may be used. Particular preference is given to using the catalysts detailed in DE-A 17 68 253.

The catalyst more preferably comprises at least one salt selected from sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate, the sodium salt of an α-hydroxycarboxylic acid, the potassium salt of an α-hydroxycarboxylic acid and/or sodium dihydrogenphosphate.

The concentration of the catalyst is generally not critical, but low concentrations can lead to a somewhat longer reaction time. High concentrations are in many cases uneconomic. In a particular aspect, the catalyst concentration may preferably be in the range of 1 to 70% by weight, more preferably 2 to 10% by weight, based on the total weight of the reaction mixture.

In a preparation of (meth)acrylic acid in batches, catalyst amounts in the range of 1 to 10% by weight, more preferably 2 to 5% by weight, may be particularly appropriate. In continuous processes, the reactant streams supplied may contain fractions of catalysts. The amounts of catalyst are preferably in the range of 0.1 to 20% by weight, more preferably in the range of 0.1 to 5% by weight. The loading of the catalyst with reactant may be within a wide range. Preference is given to using 0.01 to 10 mol, more preferably 0.05 to 1.0 mol and most preferably 0.1 to 0.5 mol of cyclic ester per mole of catalyst per hour.

The reaction is effected preferably at a temperature of 120° C. or more, more preferably at a temperature in the range of 200 to 240° C. Depending on the reaction temperature, the reaction may be performed at reduced or elevated pressure. Preference is given to performing the inventive reaction within a pressure range of 0.01-10 bar, more preferably 0.05 to 2.5 bar.

The reaction can be performed batchwise or continuously, preference being given to continuous processes.

The reaction time of the reaction depends upon factors including the cyclic esters used, the activity of the catalyst and the reaction temperature, and these parameters may be within wide ranges. The reaction time of the reaction is preferably in the range of 30 seconds to 15 hours, more preferably 15 minutes to 10 hours and most preferably 30 minutes to 5 hours.

In continuous processes, the residence time is preferably 30 seconds to 15 hours, more preferably 15 minutes to 10 hours and most preferably 30 minutes to 5 hours.

In a particular aspect of the present invention, the reaction may be performed in the presence of a polymerization inhibitor. The polymerization inhibitors useable with preference include phenothiazine, tert-butylcatechol, hydroquinone monomethyl ether, hydroquinone, 4-hydroxy-2,2,6,6-tetramethylpiperidino-oxyl (TEMPOL) or mixtures thereof; the effectiveness of these inhibitors can be improved in some cases by use of oxygen. The polymerization inhibitors may be used in a concentration in the range of 0.001 to 2.0% by weight, more preferably in the range of 0.01 to 0.2% by weight, based on the weight of the cyclic ester. Small amounts of polymerization inhibitor may also be added to the condensed (meth)acrylic acid.

The present invention is to be illustrated in detail hereinafter with reference to examples.

EXAMPLE 1

In a still, 334.75 g of tetramethylglycolide (TMG) which had been dissolved in 180.25 g of acetone were heated in the presence of the potassium salt of α-hydroxyisobutyric acid to a temperature of approx. 225° C. The loading of the catalyst was 0.57 mol of TMG per mole of catalyst per hour. The reaction was performed at standard pressure over 250 minutes. The yield of methacrylic acid was 70%.

The invention claimed is:

1. A process for preparing a (meth)acrylic acid, comprising:
    converting a cyclic ester to the (meth)acrylic acid in the presence of a catalyst to obtain a reaction mixture; and
    removing the (meth)acrylic acid from the reaction mixture in a vapor phase;
    wherein
    the catalyst is at least one alkali metal or alkaline metal salt of a carboxylic acid salt having 1 to 10 carbon atoms, a carbonate salt, a hydroxide, an oxide, a halogen salt or a sulphite salt, and
    the mole ratio of the cyclic ester to the catalyst is from 1/20 to 1/1.

2. The process according to claim 1, wherein the cyclic ester is contacted with the catalyst in the liquid phase.

3. The process according to claim 1, wherein the catalyst comprises at least one salt selected from the group consisting of sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate, the sodium salt of an α-hydroxycarboxylic acid, the potassium salt of an α-hydroxycarboxylic acid, sodium dihydrogenphosphate and combinations thereof.

4. The process according to claim 1, wherein the reaction is effected at a temperature of 120° C. or more.

5. The process according to claim 4, wherein the reaction is effected at a temperature in the range of 200 to 240° C.

6. The process according to claim 1, wherein a pressure at which the process is performed is from 0.05 bar to 2.5 bar.

7. The process according to claim 1, wherein the process is performed in the presence of a polymerization inhibitor.

8. The process according to claim 1, wherein a concentration of the catalyst is from 1 to 70% by weight based on the total weight of the reaction mixture.

9. The process according to claim 1, wherein the reaction mixture comprises a solvent.

10. The process according to claim 9, wherein said solvent is an alcohol.

11. A process for preparing a (meth)acrylate, wherein the process includes converting a cyclic ester to the (meth)acrylate according to claim 1.

12. The process according to claim 11, wherein the (meth)acrylate is methyl methacrylate.

* * * * *